United States Patent [19]

Teulon

[11] Patent Number: 4,622,328

[45] Date of Patent: Nov. 11, 1986

[54] PHENYL-NAPHTHYRIDINES AND DRUGS CONTAINING THEM, PARTICULARLY ANTI-ULCER DRUGS

[75] Inventor: Jean-Marie Teulon, La Celle Saint Cloud, France

[73] Assignee: Carpibem, France

[21] Appl. No.: 751,610

[22] Filed: Jul. 2, 1985

[30] Foreign Application Priority Data

Jul. 11, 1984 [FR] France .................................. 84 11040

[51] Int. Cl.[4] .................... A61K 31/44; C07D 47/04
[52] U.S. Cl. ..................................... 514/300; 546/122
[58] Field of Search .......................... 546/122; 514/300

[56] References Cited

U.S. PATENT DOCUMENTS 4,128,649 12/1978 Hardtmann .......................... 514/300
4,215,123 7/1980 Scotese et al. ...................... 514/300

FOREIGN PATENT DOCUMENTS 0000490 2/1979 European Pat. Off. .
0018735 11/1980 European Pat. Off. .

Primary Examiner—Henry R. Jiles
Assistant Examiner—Bernard I. Dentz
Attorney, Agent, or Firm—Scully, Scott, Murphy & Presser

[57] ABSTRACT

This invention relates to novel compounds of formula:

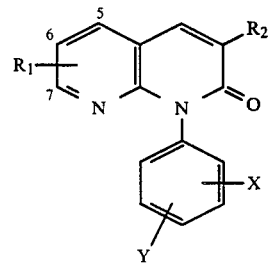

having an anti-ulcer activity.

6 Claims, No Drawings

PHENYL-NAPHTHYRIDINES AND DRUGS CONTAINING THEM, PARTICULARLY ANTI-ULCER DRUGS

The present invention relates to the phenylnaphthyridines of formula (I). It also relates to the process for preparing said products and to the applications thereof, particularly in therapeutics.

The novel compounds according to the invention are selected from the group constituted by the compounds of general formula (I):

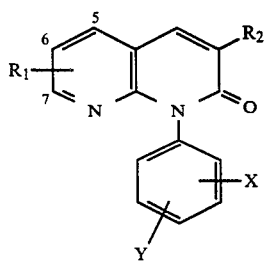

in which:
- $R_1$ represents the atom of hydrogen, a lower alkyl or cycloalkyl radical and may be in 5, 6 or 7 position of the naphthyridine; optimally, $R_1 = H$.
- $R_2$ represents the atom of hydrogen or a straight or branched lower alkyl radical; preferably, $R_2 = CH_3$
- X and/or Y represent the atom of hydrogen, a lower alkyl radical of 1 to 5 carbon atoms, a halogen, a trifluoromethyl, methoxy, nitro, thiomethyl group and may be in ortho, meta or para position on the aromatic cycle; preferably, $X = m\ CF_3$ and $Y = H$.

The compounds of formula (I) according to the invention may be synthesized: either by a Reformatsky reaction followed by a dehydration, by a Wittig reaction followed by a cyclization, or by a Perkin reaction, on an aldehyde of formula (II):

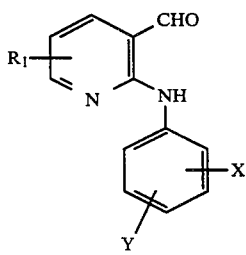

In formula (II), $R_1$, X and Y are defined as hereinabove.

Generally, the aldehydes of formula (II) may be obtained by oxidation, with the aid of a mild oxidizing agent such as for example $MnO_2$, in an organic solvent such as dichloro methane or chloroform, at a temperature of between 20° and 50° C., of an alcohol of formula (III):

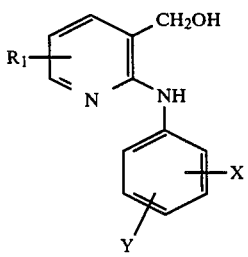

In formula (III), $R_1$, X and Y are defined as hereinabove.

The alcohols of formula (III) are obtained by reduction with the aid of a conventional reducing agent such as for example the double hydride of aluminium and lithium in an organic solvent such as for example tetrahydrofuran, of an acid or one of its esters of formula (IV):

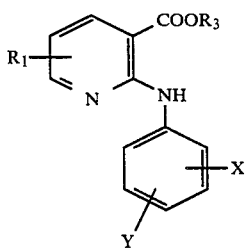

In formula (IV), $R_1$, X and Y are defined as hereinabove, $R_3$ is the atom of hydrogen or a lower alkyl of 1 to 5 carbon atoms.

The industrially preferred process for synthesis of the products of formula (I) consists in the use of the known Perkin reaction whereby an aldehyde of formula (II) is reacted on an anhydride of formula:

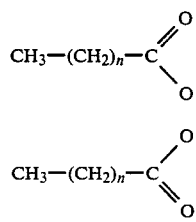

in which n is a number from 0 to 4, or on a sodium salt of the corresponding acid. The reaction may advantageously be carried out in a solvent such as methylpyrrolidone at a temperature of about 100° to 200° C.

According to the invention, therapeutic compositions useful in particular for the treatment of gastrointestinal ulcers, are proposed, characterized in that they contain, in association with a physiologically acceptable excipient, at least one compound of formula (I). Certain compounds of formula (I) further present anti-inflammatory and analgesic properties.

Other characteristics and advantages of the invention will be more readily understood on reading the following description of several examples of preparation which are in no way limiting but given by way of illustration.

Table I hereinbelow gives the structural formula of certain products.

EXAMPLE 1

[3-(trifluoromethyl)phenyl]2-amino hydroxy 3-methyl pyridine

Formula III: $R_1=Y=H$; $X=m\text{-}CF_3$

To a suspension of 52 g of double hydride of aluminium and lithium in 1000 ml of anhydrous ethyl ether, there is added drop by drop a solution of 200 g of 2-(3-trifluoromethyl phenyl amino)nicotinic acid in 500 ml of anhydrous tetrahydrofuran. At the end of the addition, the reaction mixture is heated under reflux for 3 hours. After cooling, the excess double hydride is destroyed by addition of ethyl acetate, then of a saturated aqueous solution of sodium sulfate. The precipitate formed is drained and washed with ether. The collected filtrates are evaporated in vacuo and 185.2 g of [3-(trifluoromethyl)phenyl]2-amino hydroxy 3-methyl pyridine are recovered, in the form of crystals, melting point: 103°–105° C.

The following derivatives are prepared according to this method:

6-methyl[3-(trifluoromethyl)phenyl]2-amino hydroxy 3-methyl pyridine

Formula III: $R_1=CH_3$ in 6 position; $X=H$; $X=m\text{-}CF_3$

Crystals: mp<50° C.; yield 88%

6-isopropyl[3-(trifluoromethyl)phenyl]2-amino hydroxy 3-methyl pyridine

Formula III: $R_1=$isopropyl in 6 position; $Y=H$; $X=m\text{-}CF_3$

Oil; yield 93%

6-cyclopropyl[3-(trifluoromethyl)phenyl]2-amino hydroxy 3-methyl pyridine

Formula III: $R_1=$cyclopropyl in 6 position; $Y=H$; $X=m\text{-}CF_3$

Crystals, mp=90° C.; yield 92%

[2-(methyl)3-(chloro)phenyl]2-amino hydroxy 3-methyl pyridine

Formula III: $R_1=H$; $X=o\text{-}CH_3$; $Y=m\text{-}Cl$

Crystals, mp=98°–100° C.; yield 89% phenyl 2-amino hydroxy 3-methyl pyridine

Formula III: $R_1=X=Y=H$

Oil; yield 95%

EXAMPLE 2

2-(3-trifluoromethyl phenyl amino)nicotinaldehyde

Formula II: $R_1=Y=H$; $X=m\text{-}CF_3$

To a solution of 185 g of [3-(trifluoromethyl)phenyl]2-amino hydroxy 3-methyl pyridine, prepared in Example 1 in 2300 ml of chloroform, there are added by small fractions 690 g of $MnO_2$. At the end of the addition, stirring is effected at ambient temperature for 6 hours. The reaction medium is then filtered over cellite and the filtrate is evaporated to dryness. The crystals then obtained (175 g) are recrystallized in heptane. 160 g of 2-(3-trifluoromethyl phenylamino)nicotinaldehyde are thus recovered in the form of crystals with a melting point of 80°–81° C.

The following derivatives are prepared in accordance with this method:

6-methyl 2-(3-trifluoromethyl phenylamino)nicotinaldehyde

Formula II: $R_1=CH_3$ in 6 position; $Y=H$; $X=m\text{-}CF_3$

Crystals, mp=52°–54° C.; yield 95%

6-isopropyl 2-(3-trifluoromethyl phenylamino)nicotinaldehyde

Formula II: $R_1=$isopropyl in 6 position; $Y=H$; $X=m\text{-}CF_3$

Crystals, mp<50° C.; yield 92%

6-cyclopropyl 2-(3-trifluoromethyl phenylamino)nicotinaldehyde

Formula II: $R_1=$cyclopropyl in 6 position; $Y=H$; $X=m\text{-}CF_3$

Crystals, mp=82° C.; yield 94%

2-(2-methyl 3-chloro phenylamino)nicotinaldehyde

Formula II: $R_1=H$; $X=o\text{-}CH_3$; $Y=m\text{-}Cl$

Crystals, mp=115° C.; yield 88%

2-phenylamino nicotinaldehyde

Formula II: $R_1=X=Y=H$

Crystals, mp=77°–8° C.; yield after recrystallization from 80% isopropylic ether.

EXAMPLE 3

1-(3-trifluoromethyl phenyl)1,2-dihydro 2-oxo 3-methyl 1,8-naphthyridine

Formula I: $R_1=Y=H$; $X=m\text{-}CF_3$; $R_2=CH_3$

A solution of 50 g of 2-(3-trifluoromethyl phenyl amino)nicotinaldehyde synthesized as in Example 2, 28 ml of 2-bromo propionate of ethyl in 200 ml of anhydrous benzene is prepared. 20 ml of this solution are poured over 16 g of activated zinc powder. By heating, the Reformatsky reaction starts up, then the rest of the solution is added so that the reflux is maintained. At the end of the addition, the reflux is maintained for 2 hours.

The reaction mixture is then cooled then hydrolyzed by dilute sulfuric acid.

The organic phase being separated, the mother liquors are extracted with chloroform. The organic phases are dried over sodium sulfate, then concentrated in vacuo. The residue obtained, 60 g is taken up in 400 ml of toluene and 20 ml of $POCl_3$, then heated under reflux for 2 hours. After cooling, the organic phase is washed in water, then dried and concentrated in vacuo. A residue of 35 g is thus obtained which crystallizes. After recrystallization from isopropanol, 24 g of 1-(3-trifluoromethyl phenyl)1,2-dihydro 2-oxo 3-methyl 1,8-naphthyridine are recovered, in the form of crystals, mp: 189°–190° C.

EXAMPLE 4

1-(3-trifluoromethyl phenyl)1,2-dihydro 2-oxo 1,8-naphthyridine

Formula I: $R_1=R_2=Y=H$; $X=m\text{-}CF_3$

According to the modus operandi of Example 3, but using 43.5 of 2-(3-trifluoromethyl phenyl amino)nicotinaldehyde prepared as in Example 2 and 23 ml of ethyl bromoacetate, 15 g of 1-(3-trifluoromethyl phenyl)1,2-dihydro 2-oxo 1,8-naphthyridine are obtained, after recrystallization from isopropanol, in the form of crystals, mp 159°–160° C.

EXAMPLE 5

1-(3-trifluoromethyl phenyl)1,2-dihydro 2-oxo 3-ethyl 1,8-naphthyridine

Formula I: $R_1=Y=H$; $X=m\text{-}CF_3$; $R_2=C_2H_5$

According to the modus operandi of Example 3, but using 30 g of 2-(3-trifluoromethyl phenyl amino)nicotinaldehyde prepared as in Example 2 and 19.2 ml of 2-bromo butyrate of ethyl, 8 g of 1-(3-trifluoromethyl phenyl) 1,2-dihydro 2-oxo 3-ethyl 1,8-naphthyridine are obtained, after recrystallization from isopropanol, in the form of crystals, mp: 144°–146° C.

The following derivatives are prepared, still according to this modus operandi:

EXAMPLE 6

1-(3-trifluoromethyl phenyl)1,2-dihydro 2-oxo 3,7-dimethyl 1,8-naphthyridine

Formula I: Y=H; X=m-$CF_3$; $R_1$=$R_2$=$CH_3$
Crystals, mp=158° C. (isopropanol); yield: 35%

EXAMPLE 7

1-(3-trifluoromethyl phenyl)1,2-dihydro 2-oxo 3-methyl 7-isopropyl 1,8-naphthyridine Formula I: Y=H; X=m-$CF_3$; $R_1$=isopropyl; $R_2$=$CH_3$
Crystals, mp=115° C. (hexane); yield: 30%

EXAMPLE 8

1-(3-trifluoromethyl phenyl)1,2-dihydro 2-oxo 3-methyl 7-cyclopropyl 1,8-naphthyridine Formula I: Y=H; X=m-$CF_3$; $R_1$=cyclopropyl; $R_2$=$CH_3$
Crystals, mp=147° C. (isopropanol); yield 32%

EXAMPLE 9

1-(2-methyl 3-chloro phenyl)1,2-dihydro 2-oxo 3-methyl 1,8-naphthyridine

Formula I: X=o-$CH_3$; Y=m-Cl; $R_1$=H; $R_2$=$CH_3$
Crystals, mp=192° C. (isopropanol); yield: 25%

EXAMPLE 10

1-(3-trifluoromethyl phenyl)1,2-dihydro 2-oxo 3-methyl 1,8-naphthyridine

Formula I: $R_1$=Y=H; X=m-$CF_3$; $R_2$=$CH_3$

A mixture of 20 g of 2-(3-trifluoromethyl phenylamino)nicotinaldehyde synthesized as in Example 2, 10 g of sodium propioniate and 20 ml of propionic anhydride, is heated under reflux for 1 hr. 15 mins.

The reaction mixture is then cooled, 100 ml of water are added thereto and the mixture is stirred for 30 mins. at ambient temperature. It is extracted with dichloromethane, the organic phase is washed with water, with a 10% sodium hydroxide solution then again with water, dried over sodium sulfate and concentrated in vacuo. The residue obtained crystallizes in pentane, the crystals are drained, washed with isopropylic ether and dried. The 17.6 g of crystals obtained are recrystallized from isopropanol leading to 14.3 g of 1-(3-trifluoromethyl phenyl)1,2-dihydro 2-oxo 3-methyl 1,8-naphthyridine, in the form of crystals with a melting point of 189°–190° C., identical to those described in Example 3.

The following derivative is prepared according to his method.

EXAMPLE 11

1-phenyl 1,2-dihydro 2-oxo 3-methyl 1,8-naphthyridine

Formula I: $R_1$=X=Y=H; $R_2$=$CH_3$
Crystals, mp=217°–8° C. (ethanol); yield: 56%

The following compounds were prepared according to a similar process:

2-(3-nitro phenyl amino)hydroxy 3-methyl pyridine
Formula III: $R_1$=Y=H; X=m-$NO_2$
Crystals, mp=150°–5° C.; yield: 84%

2-nitro phenyl amino)nicotinaldehyde
Formula II: $R_1$=Y=H; X=m-$NO_2$
Crystals, mp=160°–2° C. (acetonitrile); yield: 70%

EXAMPLE 12

The process of Example 10 was reproduced to prepare:

1-(3-nitro phenyl)1,2-dihydro 2-oxo 3-methyl 1,8-napthyridine

Formula I: $R_1$=Y=H; X=m-$NO_2$; $R_2$=$CH_3$
Crystals, mp=231°–2° C. (acetonitrile); yield: 52%

EXAMPLES 13 AND 14

By operating as in the preceding Examples, the following compounds have been prepared:

2-(3-methoxy phenyl)amino hydroxy 3-methyl pyridine
Formula III: $R_1$=Y=H; X=m-$OCH_3$
Crystals, mp=94°–95° C.; yield: 98%

2-(4-methyl phenyl)amino hydroxy 3-methyl pyridine
Formula III: $R_1$=Y=H; X=p-$CH_3$
Thick oil; yield: 98%

2-(3-methoxy phenyl amino)nicotinaldehyde
Formula II: $R_1$=Y=H; X=m-$OCH_3$
Crystals, mp=65°–66° C. (isopropylic ether); yield: 75%

2-(4-methyl phenyl amino)nicotinaldehyde
Formula II: $R_1$=Y=H; X=p-$CH_3$
Crystals, mp=55°–8° C. (isopropylic ether); yield: 72% which made it possible, by carrying out Example 10, to prepare the following compounds:

EXAMPLE 13

1-(3-methoxy phenyl)1,2-dihydro 2-oxo 3-methyl 1,8-naphthyridine

Formula I: $R_1$=Y=H; X=m-$OCH_3$; $R_2$=$CH_3$
Crystals, mp=196°–197° C. (isopropanol); yield: 40%

EXAMPLE 14

1-(4-methyl phenyl)1,2-dihydro 2-oxo 3-methyl 1,8-naphthyridine

Formula I: $R_1$=Y=H; X=p-$CH_3$; $R_2$=$CH_3$
Crystals, mp=212°–213° C. (isopropanol); yield: 39%

The pharmacological properties of the products according to the invention have been studied.

Anti-Ulcer Activity

Method

Batches of 10 to 30 male rats of OFA (Iffa Credo) strain, weighing 160-180 g, are placed on a water diet 24 hours before the oral administration of the product studied. Thirty minutes later, a medicamentous ulcer-forming agent or a necrosing agent (for example absolute ethanol) is administered by the oral route at doses which cause in the control animals a maximum gastric ulceration. The stomachs are removed, according to the test, 6 and 1 hr. respectively after the last treatment. The gastric lesions are then assessed macroscopically (dimensioning and measurement of the size of the ulcers).

Results

They are expressed in the form of % of inhibition of the ulcers. The active dose 50 is determined graphically.

| Dose | % of protection of lesions provoked | | | | | |
|---|---|---|---|---|---|---|
| | (1) administration of a medicamentous ulcer forming agent | | | (2) administration of a necrosing agent | | |
| mg·kg⁻¹ VO | Examples 3 & 10 | Example 4 | Example 11 | Examples 3 & 10 | Example 4 | Example 11 |
| 0.06 | | | | 0 | | 86 |
| 0.125 | | | | 17 | | |
| 0.25 | — | | 1 | 42 | | 95 |
| 0.5 | | | 34 | 64 | | |
| 1 | | | 75 | 79 | 6 | 94 |
| 2 | 15 | | 100 | | 52 | |
| 4 | 22 | 11 | | | 87 | 98 |
| 8 | 62 | 40 | | | | |
| 16 | 87 | 68 | | | | |
| 32 | 95 | 81 | | | | |
| 64 | | | | | | |
| 256 | | | | | | |
| AD50 mg·kg⁻¹ VO | 6.5 | 12 | 0.67 | 0.37 | 2.2 | <0.06 |

(1) non-steroid anti-inflammatory agent
(2) ethanol

Anti-Secretory Activity

Method

A pyloric ligature is made under ether anaesthesia on batches of 5 male rats of OFA (Iffa Credo) strain weighing 180–200 g. The product studied is administered by the oral or sub-cutaneous route at the time of the ligature. The animals are sacrificed 4 hours later and the acidity of the gastric fluid collected is titered by 0.1N sodium hydroxide to pH 4 and 7.

Results

They are expressed in percentage of inhibition of the total acid secretion. The active dose 50 is determined from the linear regression. The significance is given by the Student "t" test (* and ** for $p<0.05$ and $p<0.01$).

| Dose mg·kg⁻¹ VO | % of inhibition of the total acid secretion | | |
|---|---|---|---|
| | Administered VO | Administered SC | |
| | Examples 3 & 10 | Examples 3 & 10 | Example 11 |
| 0.03 | | | 37 |
| 0.06 | | | 46 |
| 0.125 | 2 | | 63* |
| 0.25 | 18 | 4 | 76** |
| 0.5 | 59* | 38 | 81** |
| 1 | 56 | 65** | |
| 2 | 75** | 90** | |
| AD50 mg·kg⁻¹ VO | 0.70 (0.34–1.44) | 0.72 (0.44–1.18) | 0.065 (0.032–0.135) |

Anti-Inflammatory Activity

Method

Batches of 6 to 12 male rats of CD (Charles River) strain, weighing 120–130 g, receive for food and drink a 9 o/oo solution of sodium chloride and 200 o/oo of glucose 18 hours before the test.

The product studied is administered by the oral route at two goes: a half-dose 2 hours and a half-dose 30 minutes before sub-cutaneous injection, in the plantar pad of a rear paw, of 0.05 ml of a 1.5% aqueous solution of carragenin. The volume of the paw is measured by plethysmography at regular intervals.

Results

The table gives the percentages of inhibition of the oedema of the maximum of its amplitude in the controls. The active dose 50 and its limits are determined from the linear regression. The significance of the results is given by the Student "t" test (*,  and * for $p<0.05$, $p<0.01$ and $p<0.0001$).

| Dose mg·kg⁻¹ VO | % of inhibition of the oedema | |
|---|---|---|
| | Examples 3 and 10 | Example 4 |
| 4 | 10 | 14 |
| 16 | 31* | 21 |
| 64 | 47*** | 80*** |
| 128 | 61*** | 70*** |
| 256 | 64*** | 83*** |
| AD50 mg·kg⁻¹ VO | 73.3 (47.6–112.9) | not calculatable |

Analgesic Activity

Method

Batches of 6 to 18 male mice of CD1 (Charles River) strain, weighing 18 to 22 g, receive by the intraperitoneal route a water-alcohol 0.02% solution of phenylbenzoquinone 1 hour after treatment by the oral route. The number of painful reactions is counted from the 5th to the 10th minute.

Results

The following table gives the percentage of inhibition of the twists and stretches. The active dose and its limits are determined from the linear regression.

| Dose mg·kg⁻¹ VO | % of inhibition of the painful reactions | |
|---|---|---|
| | Examples 3 and 10 | Example 4 |
| 8 | 6 | |
| 16 | 30** | 6 |
| 32 | 26* | 39* |
| 64 | 57*** | 37* |
| 128 | 58*** | 79*** |
| 256 | 73*** | 93*** |
| DA50 | 69.4 | 62.0 |

-continued

| Dose | % of inhibition of the painful reactions | |
|---|---|---|
| mg · kg − 1 VO | Examples 3 and 10 | Example 4 |
| mg · kg − 1 VO | (45.7–105.5) | (46.8–82.0) |

Toxicology

Toxicological studies made in the fasting Sprague Dawley rat after administration by the oral route, have shown that the products according to the Examples have an $LD_{50}$ greater (products of Examples 3, 10 and 4) or equal (product of Example 11) to 256 mg.kg-1.

In conclusion, it appears that the products according to the invention and their non-toxic addition salts may advantageously be used as active ingredients in drugs administered by the oral or injectable route. Said drugs will contain from 200 to 600 mg of active ingredient and may be used for the treatment of gastrointestinal ulcers.

TABLE I 5145-01 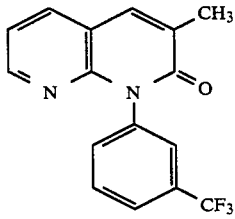 Examples 3 & 10

5145-02 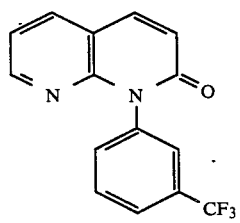 Example 4

5145-11 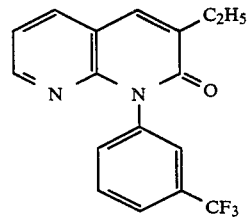 Example 5

5145-05 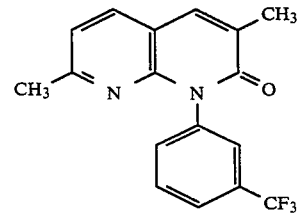 Example 6

TABLE I-continued 5145-07 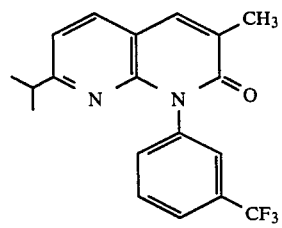 Example 7

5145-08 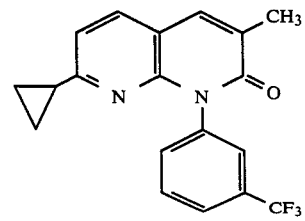 Example 8

5145-04 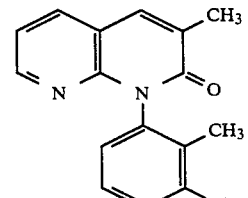 Example 9

5145-12 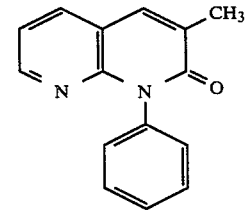 Example 11

5145-14 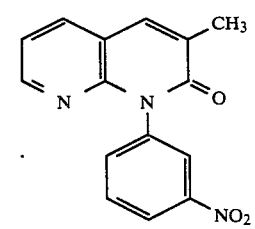 Example 12

What is claimed is:

1. A compound of the formula:

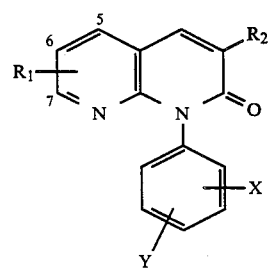

in which:
R₁ represents hydrogen, a lower alkyl or cycloalkyl radical and may be in 5, 6 or 7 position of the naphthyridine;

$R_2$ represents hydrogen, a straight or branched lower alkyl radical;

X and/or Y represent hydrogen, a lower alkyl radical of 1 to 5 carbon atoms, a halogen, a trifluoromethyl, methoxy, nitro, thiomethyl group and may be in ortho, meta or para position on the aromatic ring.

2. A compound of claim 1, wherein $R_2=CH_3$.

3. A compound of claim 1, wherein $R_1=H$.

4. A compound of claim 1 selected from the group consisting of:

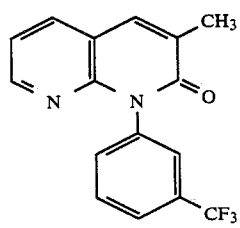

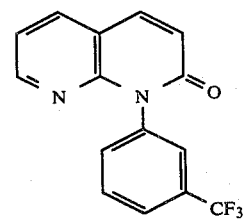

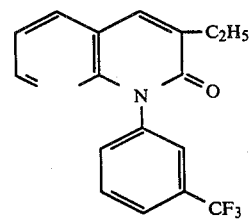

5. A compound of claim 1, wherein $R_1=H$ and $R_2=CH_3$.

6. A pharmaceutical composition in dosage unit form useful for the treatment of gastrointestinal ulcers, inflammatory conditions and analgesia comprising from about 200 to 600 milligrams of at least one compound of any one of claims 1 to 4 or 5 in association with a physiologically acceptable excipient.

* * * * *